United States Patent [19]
Forbes et al.

[11] Patent Number: 5,866,586
[45] Date of Patent: Feb. 2, 1999

[54] CNS-ACTIVE PYRIDINYLUREA DERIVATIVES

[75] Inventors: Ian Thomson Forbes, Stevenage; Graham Elgin Jones, Hertford, both of England

[73] Assignee: SmithKline Beecham p.l.c., Brentford, England

[21] Appl. No.: 817,580

[22] PCT Filed: Oct. 5, 1997

[86] PCT No.: PCT/EP95/03944

§ 371 Date: Apr. 17, 1997

§ 102(e) Date: Apr. 17, 1997

[87] PCT Pub. No.: WO96/11930

PCT Pub. Date: Apr. 25, 1996

[30] Foreign Application Priority Data

Oct. 18, 1994 [GB] United Kingdom ............ 9420999

[51] Int. Cl.[6] ............ C07D 471/04; C07D 213/75; A61K 31/44
[52] U.S. Cl. .......... 514/300; 514/254; 514/332; 544/300; 546/113; 546/255
[58] Field of Search .............. 546/113, 255; 514/300, 332, 254; 544/300

[56] References Cited

FOREIGN PATENT DOCUMENTS

| WO 94/04533 | 3/1994 | WIPO . |
| WO 94/14801 | 7/1994 | WIPO . |
| WO94/18972 | 9/1994 | WIPO . |

OTHER PUBLICATIONS

Stanovnik, et al., "Heteroacyl Azides as Acylating Agents for Aromatic or Heteroaromatic Amines (1)", J. Heterocyclic Chem., vol. 17, pp. 733–736, 1980.

*Primary Examiner*—Zinna Northington Davis
*Attorney, Agent, or Firm*—Linda E. Hall; Stephen A. Venetianer

[57] ABSTRACT

The invention relates to heterocyclic compounds of formula (I) having pharmacological activity, processes for their preparation, to compositions containing them and to their use in the treatment of CNS disorders, wherein P represents phenyl, a quinoline or isoquinoline residue, or a 5-membered or 6-membered aromatic heterocyclic ring containing up to three heteroatoms selected from nitrogen, oxygen or sulphur; $R^3$ is a group of formula (i) or (ii).

9 Claims, No Drawings

CNS-ACTIVE PYRIDINYLUREA DERIVATIVES

This application is a 371 of PCT/EP95/03944 filed Oct. 5, 1995.

This invention relates to compounds having pharmacological activity, processes for their preparation, to compositions containing them and to their use in the treatment of CNS disorders.

WO 94/04533 (SmithKline Beecham plc) describes indole and indoline derivatives which are described as possessing $5HT_{2C}$ receptor antagonist activity. A structurally distinct class of compounds has now been discovered, which have been found to have $5HT_{2C}$ receptor antagonist activity. Some or all of the compounds of the invention also exhibit $5HT_{2B}$ antagonist activity. $5HT_{2B/2C}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

The present invention therefore provides, in a first aspect, a compound of formula (I) or a salt thereof:

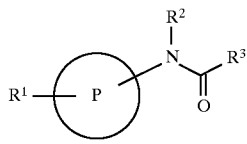

wherein:

represents phenyl, a quinoline or isoquinoline residue, or a 5-membered or 6-membered aromatic heterocyclic ring containing up to three heteroatoms selected from nitrogen, oxygen or sulphur;

$R^1$ is hydrogen, $C_{1-6}$ alkyl, $C_{1-6}$ alkylthio, cyano, nitro, halogen, $CF_3$, $NR^8R^9$, $CONR^8R^9$, $CO_2R^{10}$ or $OR^{10}$ where $R^8$, $R^9$ and $R^{10}$ are independently hydrogen, $C_{1-6}$ alkyl or aryl $C_{1-6}$ alkyl;

$R^2$ is hydrogen or $C_{1-6}$ alkyl;

$R^3$ is a group of formula (i):

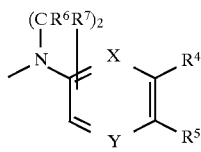

in which:

X and Y are both nitrogen or one is nitrogen and the other is carbon or a CH group;

$R^4$ and $R^5$ groups are independently $C_{1-6}$ alkyl optionally substituted by one or more halogen atoms, $C_{2-6}$ alkenyl, $C_{3-6}$ cycloalkyloxy, $C_{3-6}$ cycloalkyl$C_{1-6}$ alkoxy, $C_{2-6}$ alkynyl, $C_{3-6}$ cycloalkyl, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$ alkoxy, hydroxy, halogen, nitro, $CF_3$, $C_2F_5$, $OCF_3$, $SCF_3$, $SO_2CF_3$, $SO_2F$, formyl, $C_{2-6}$ alkanoyl, cyano, optionally substituted phenyl or thienyl, $NR^8R^9$, $CONR^8R^9$, or $OR^{10}$ where $R^8$, $R^9$ and $R^{10}$ are as defined for $R^1$, $CO_2R^{11}$ where $R^{11}$ is hydrogen or $C_{1-6}$ alkyl; or $R^4$ and $R^5$ form part of an optionally substituted 5-membered carbocyclic or heterocyclic ring;

$R^6$ and $R^7$ are independently hydrogen or $C_{1-6}$ alkyl; or $R^3$ is a group of formula (ii):

in which $R^4$ and $R^5$ are as defined in formula (i), X and Y are both nitrogen or one is nitrogen and the other is a CH group;

and $R^{12}$ is hydrogen or $C_{1-6}$ alkyl.

$C_{1-6}$ alkyl groups, whether alone or as part of another group, may be straight chain or branched.

The urea moiety can be attached to a carbon or any available nitrogen atom of the ring P, preferably it is attached to a carbon atom. Suitable moieties when the ring P is a 5-membered aromatic heterocyclic ring include isothiazolyl, isoxazolyl, thiadiazolyl and triazolyl. Suitable moieties when the ring P is a 6-membered aromatic heterocyclic ring include, for example, pyridyl, pyrimidyl or pyrazinyl. When P is quinoline, or an isoquinoline residue, the urea moiety can be attached at any position of the ring, preferably to the 4- or 5-position. Preferably P is 3-pyridyl.

Preferably $R^1$ is hydrogen.

Preferably $R^2$ is hydrogen.

Preferably $R^3$ is a group of formula (i) where $R^6$ and $R^7$ are hydrogen and X is carbon or a CH group and Y is nitrogen.

Preferably $R^4$ is trifluoromethyl or halogen. Most preferably $R^4$ is halogen, in particular chloro.

Preferably $R^5$ is $C_{1-6}$ alkylthio, in particular thiomethyl, or $C_{1-6}$ alkoxy, in particular methoxy. Most preferably $R^4$ is thiomethyl.

When $R^4$ and $R^5$ form part of an aromatic ring suitable rings include thiophene, furan and pyrrole rings. Optional subtituents for such rings include $C_{1-6}$ alkyl groups, for example methyl.

Particular compounds of the invention include:
N-3-Pyridyl-N'-5-(2-thiomethyl-3-chloro)pyridyl urea,
4-Chloro-5-methylthio-2,3-dihydropyrrolo[2,3-c]pyridine-1-carboxylic acid pyridin-3-yl amide,
6-Chloro-5-methylthio-2,3-dihydropyrrolo[3,2-b]pyridine-1-carboxylic acid pyridin-3-yl amide,
and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicyclic, citric, lactic, mandelic, tartaric and methanesulphonic.

Certain compounds of formula (I) may also form N-oxides or solvates such as hydrates, and the invention also extends to these forms. When referred to herein, it is understood that the term 'compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

the coupling of a compound of formula (II);

with a compound of formula (III)

wherein P is as defined in formula (I), A and B contain the appropriate functional group(s) necessary to form the moiety —$NR^{2'}CO$ when coupled, the variables $R^{1'}$, $R^{2'}$ and $R^{3'}$ are $R^1$, $R^2$ and $R^3$ respectively, as defined in formula (I), or groups convertible thereto, and thereafter optionally and as necessary and in any appropriate order, converting any $R^{1'}$, $R^{2'}$ and $R^{3'}$, when other than $R^1$, $R^2$ and $R^3$ respectively to $R^1$, $R^2$ and $R^3$, interconverting $R^1$, $R^2$ and $R^3$ and forming a pharmaceutically acceptable salt thereof.

Suitable examples of groups A and B include;
 (i) A is —$N{=}C{=}O$ and B is hydrogen,
 (ii) A is -$NR^{2'}COL$ and B is hydrogen,
 (iii) A is $NHR^{2'}$ and B is COL, or
 (iv) A is $NHR^{2'}$ and B completes an isocyanate group
 (v) A is halogen and B is $CONHR^{2'}$
wherein $R^{2'}$ is as defined above and L is a leaving group. Examples of suitable leaving groups L include halogen such as chloro, bromo, imidazole, phenoxy or phenylthio optionally substituted, for example, with halogen.

When A is —$N{=}C{=}O$ and B is hydrogen the reaction is suitably carried out in an inert solvent for example dichloromethane or toluene at ambient or elevated temperature.

When A is —NR2'COL and B is hydrogen or when A is —NHR2'and B is —COL, the reaction is suitably carried out in an inert solvent such as dichloromethane at ambient temperature optionally in the presence of a base, such as triethylamine or in dimethylformamide at ambient or elevated temperature.

When A is halogen and B is $CONHR^{2'}$, the reaction is suitably carried out in an inert solvent such as toluene at elevated temperature, optionally in the presence of a base.

It should be appreciated that P in formula (I) represents rings P as defined in relation to formula (I) in which $R^1$ is as defined in relation to formula (I) or groups convertible thereto i.e. $R^{1'}$.

$R^4$ and $R^5$ groups can be introduced at any suitable stage in the process, preferably $R^4$ and $R^5$ groups are introduced at any early stage in the process. It should be appreciated that it is preferred that the groups $R^1$, $R^2$, $R^4$ and $R^5$ are introduced before coupling compounds of formula (II) and (III).

Suitable examples of groups convertible to alkyl groups include acyl groups which are introduced conventionally and may be converted to the corresponding alkyl group by conventionally reduction, such as using sodium borohydride in an inert solvent followed by hydrogenolysis in an inert solvent. Hydrogen substituents may be obtained from alkoxycarbonyl groups which may be converted to hydrogen by hydrolysis and decarboxylation.

Suitable examples of a group $R^{2'}$ which are convertible to $R^2$, include alkoxycarbonyl and benzyl orparamethoxybenzyl which are converted to the group where R2 is hydrogen using conventional conditions.

Interconversions of $R^1$, $R^2$ and $R^3$ are carried out by conventional procedures. For example $R^1$ halo may be introduced by selective halogenation of the ring P using conventional conditions. It should be appreciated that it may be necessary to protect any hydrogen variables which are not required to be interconverted.

Suitable protecting groups and methods for their attachment and removal are conventional in the art of organic chemistry, such as those described in Green T. W. 'Protective groups in organic synthesis' New York, Wiley (1981).

Compounds of formula (II) in which A is NHR2' are known compounds or can be prepared analogously to known compounds, see, for example, WO92/05170 (SmithKline Beecham plc).

Compounds of formula (II) in which A is —$N{=}C{=}O$ may be prepared by treating a compound of formula (II) in which:
 i) A is amino, which phosgene or a phosgene equivalent, in the presence of excess base in an inert solvent.
 ii) A is acylazide (i.e. $CON_3$), via the nitrene, by thermal rearrangement using conventional conditions (ref L.S. Trifonov et al, Helv. Chim. Acta 1987 70 262).
 iii) A is $CONH_2$, via the nitrene intermediate using conventional conditions.

Compounds of formula (II) in which A is $NR^{21}COL$ may be prepared by reacting a compound of formula (II) in which A is $NHR^{2'}$ with phosgene or a phosgene equivalent in an inert solvent, at low temperature, if necessary in the presence of one equivalent of a base such as trithylamine.

Compounds of formula (III) may be prepared according to known method or analogous to known methods, for example
 a) when $R^{3'}$ is a group of formula (i), from the appropriate pyridine carboxylic acid via azide formation and conversion to the corresponding isocyanate.
 b) when $R^{3'}$ is a group of formula (ii), from the appropriate nitropyridine the substitution of an ortho position with a functionalised alkyl group. It will be appreciated that cyclisation to form a fused dihydropyrrole ring can be undertaken at an intermediate stage or subsequent to urea formation.

Compounds of formula (II) in which A is halogen and $R^{1'}$ is hydrogen are commercially available.

Novel intermediates of formula (III) also form part of the invention.

Pharmaceutically acceptable salts may be prepared conventionally by reaction with the appropriate acid or acid derivative. N-oxides may be formed conventionally by reaction with hydrogen peroxide or percarboxylic acids.

Compound of formula (I) and their pharmaceutically acceptable salts have $5HT_{2B/2C}$ receptor antagonist activity and are believed to be of potential use in the treatment or prophylaxis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administerable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealant. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 66% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxilogical effects are expected with the compounds of the invention.

The following Descriptions and Examples illustrate the preparation of compounds of the invention.

Description 1

3-Chloro-2-thioxo-1,1-dihydropyridine-5-carboxylic acid (D1)

5,6 Dichloronicotinic acid (5 g 0.026 mole) in ethanol (150 ml) was treated with thiourea (2.15 g, 0.029 mole) and heated under reflux for 1½ hours. After cooling to room temperature the solvent was removed in vacuo and the residue heated to 100° C. in 10% aqueous NaOH solution (100 ml) for 2 hours. After cooling to room temperature, 2.5 HC was added until acidic and the title compound (4.28 g, 87%) was isolated by filtration as a yellow solid and dried in vacuo.

$^1$HNMR (250 MHz; $D_6$DMSO) $\delta$8.5 (s, 3H), 14.02–14.59 (br s, 1H)

Description 2

Methyl 3-chloro-2-thiomethylpyridine-5-carboxylate (D2)

3-Chloro-2-thioxo-1,2-dihydropyridine-5-carboxylic acid (1D) (4.2 g, 0.023 mole) in dry DMF (60 ml) under argon was treated portionwise with sodium hydride (1.38 g of and 80% dispersion in oil, 0.046 mole) and stirred at room temperature for 2 hours. Iodomethane (2.87 ml, 0.046 mole) was added and the mixture stirred for 1¼ hours. The solvent was removed in vacuo and the residue partitioned between water and ethyl, and the ethyl acetate layer dried ($Na_2SO_4$) and evaporated in vacuo. The residue was flash columned in $SiO_2$ eluting with $CH_2Cl_2$ to leave the title compound as a cream solid (2.5 g, 50%).

$^1$HNMR (250 MHz, $CECl_3$) $\delta$: 2.61 (s, 3H), 3.93 (s,3H), 8.10 (d, 1H), 8.95 (d, 1H).

Description 3

3-Chloro-2-thiomethylpyridine-5-carboxylic acid hydrazide (D3)

Methyl 3-chloro-2-thiomethylpyridine-5-carboxylate (D2) (1.5 g, 0.006 mole) in methanol (150 ml) was treated with hydrazine monohydrate (1.0 ml, 0.021 mole) and heated under reflux overnight. After cooling to room temperature the solvent was removed in vacuo and the residue triturated with $H_2O$, filtered, washed with water and the residue triturated in ethyl acetate, filtered and dried in vacuo to leave the title compound as a white solid (0.45 g, 32%).

$^1$HNMR (250 MHz; DMSO) $\delta$: 2.59 (s,3H), 4.58 (s,2H), 8.16(d,1H), 8.85 (d,1H), 9,95 (s,1H)

Description 4

3-Chloro-2-thiomethylpyridine-5-carboxylic acid azide (D4)

3-Chloro-2-thiomethylnicotinic acid hydrazide (D3) (0.45 g, 0.002 mole) was suspended in $H_2O$ (1.5 ml) and conc HCl was added until a homogeneous solution was obtained. The solution was cooled to 0° C. and a solution of sodium nitrite (0.17 g, 0.0025 mole) in $H_2O$ (2 ml) was added dropwise and the mixture allowed to warm to room temperature. The title compound (0.33 g, 72% was filtered, washed with $H_2O$ and dried in vacuo.

$^1$H NMR (250 MHz; $CDCl_3$) $\delta$: 2.62(s,3H), 8.08 (d, 1H), 8.92 (d,1H).

Description 5

3-Chloro-2-methylthio-5-nitropyridine (D5)

2,3-Dichloro-5-nitropyridine (7.90 g, 0.041 mol) (Synthesis, 1990, 499) was dissolved in ethanol (150 ml) and was treated with thiourea (3.43 g, 0.045 mol). The resultant mixture was then heated to reflux with stirring under argon. After 3 h, the reaction mixture was allowed to cool, and was left stirring at room temp. for 16 h. 10% Sodium hydroxide solution (160 ml) was then added and the reaction mixture was heated to reflux with stirring. After 1 h, the reaction mixture was cooled to 10° C., and methyl iodide (2.80 ml, 0.045 mol) was added. After 1 h, the resultant precipitate was filtered off to give the title compound as an orange solid (5.90 g, 70%).

$^1$ H NMR (200 MHz, CDCl$_3$) δ(ppm): 9.20 (d, 1H), 8.70 (d,1H), 2.70 (s, 3H).

Description 6

3-Chloro-4-methyl-2-methylthio-5-nitropyridine (A) and 3-Chloro-6-methyl-2-methylthio-5-nitropyridine (B) (D6)

5 3-Chloro-2-methylthio-5-nitropyridine (D5) (5.50 g, 0.027 mol) was dissolved in dry THF (180 ml) and was cooled to –25° C. with stirring under argon. Methylmagnesium bromide (3M in Et$_2$O) (13.5 ml, 0.041 mol) was then added slowly. The mixture was maintained at –25° C. for 0.5 h before DDQ (7.34 g, 0.032 mol) was added. The mixture was then allowed to warm to room temperature and after 0.5h was diluted with diethyl ether (300 ml) and was washed with sodium bicarbonate solution. The organic layer was then dried (Na$_2$SO$_4$) and evaporated under reduced pressure to give a brown oil, which was dried in vacuo. The oil was purified by silica gel chromatography (10:1 Petrol : Et$_2$O as eluant) to give the title compounds (4.16 g, 70%) as a 1:1.6, (A): (B) mixture by $^1$H NMR.

$^1$H NMR (250 MHz, CDCl$_3$) δ(ppm): 8.90 (s, 0.4H), 8.22 (s, 0.6H), 2.88 (s, 1.8H), 2.58 (s, 1.2H), 2.54 (s, 1.8H), 2.49 (s, 1.2H).

Description 7

3-Chloro-4-(2-hydroxyethyl)-2-methylthio-5-nitropyridine (A) and 3-Chloro-6-methyl-2-methylthio-5-nitropyridine (B) (D7)

The mixture of products from description 6 (4.14 g, 0.019 mmol) was dissolved in dry DMSO (120 ml) and paraformaldehyde (0.555 g, 0.018 mol) was added, followed by potassium hydroxide (0.32M in EtOH) (5.50 ml, 0.0018 mol) dropwise. After 3 h, the reaction mixture was diluted with water (~500 ml) and then was extracted with ethyl acetate (2×200 ml). The combined organic layers were then washed with water (4×), dried (Na$_2$SO$_4$) and evaporated under reduced pressure to give an orange oil, that was purified by SiO$_2$ chromatography (3:1, Petrol : Et$_2$O as eluant) to give the title compound (B) as the first eluted component (1.36 g, 33%) and the title compound (A) as the second eluted component (1.00 g, 21%).

(A) $^1$H NMR (250 MHz, CDCl$_3$) δ(ppm): 8.90 (s, 1H), 3.97 (q, 2H), 3.42 (t, 2H), 2.60 (s, 3H), 1.70 (t, 1H). (B) $^1$H NMR (250 MHz, CDC$_3$) δ(ppm): 8.70 (s, 1H), 2.88 (s, 3H), 2.52 (s, 3H)

Description 8

5-Amino-3-chloro-4-(2-hydroxyethyl)-2-methylthiopyridine (D8)

3-Chloro-4-(2-hydroxyethyl)-2-methylthio-5-nitropyridine (0.430 g, 1.73 mmol) was dissolved in a mixture of glacial acetic acid (30 ml) and water (15 ml), and was treated with iron powder (3.78 g, 0.068 mol) with stirring. After 0.5 h, the mixture was filtered through kieselguhr and the resultant yellow solution was evaporated under reduced pressure. The residue was partitioned between sodium bicarbonate solution and ethyl acetate. The biphasic suspension was filtered through kieselguhr, and the organic layer was dried (Na$_2$SO$_4$) and evaporated under reduced pressure to give the title compound as a yellow solid, which was dried in vacuo (0.275 g, 73%).

$^1$H NMR (250 MHz, CDCl$_3$) δ(ppm): 7.90 (s, 1H), 4.00 (br s, 2H), 3.97 (t, 2H), 3.02 (t, 2H), 2.40 (s, 3H).

Description 9

N-3-[5-Chloro-4-(2-hydroxyethyl)-6-methylthio]pyridyl-N'-(3-pyridyl)urea (D9)

Nicotinoyl azide (0.274 g, 1.85 mmol) was dissolved in toluene (10 ml) and heated to reflux. After ½ h the reaction mixture was allowed to cool and was added to a stirred solution of 5-amino-3-chloro-4-(2-hydroxyethyl)-2-methylthiopyridine (D8) (0.370 g, 0.67 mmol) in dichloromethane (50 ml). After 1 h, the dichloromethane was removed by evaporation under reduced pressure and the resultant precipitate was filtered off and dried in vacuo to give the title compound as a cream solid (0.438 g, 77%).

$^1$H NMR (200 MHz, CD$_3$SOCD$_3$) δ(ppm): 9.52 (s, 1H), 8.70 (s, 1H), 8.53 (d, 1H), 8.29 (s, 1H), 8.20 (dd, 1H), 7.97 (dd, 1H), 7.32 (dd, 1H), 5.20 (t, 1H), 3.70 (q, 2H), 2.97 (t, 2H), 2.50 (s, 3H)

Description 10

3-Chloro-6-[2-(dimethylamino)ethenyl]-2-methylthio-5-nitropyridine (D10)

3-Chloro-6-methyl-2-methylthio-5-nitropyridine (D7) (1.35 g, 6.18 mmol) was treated with tert-butoxy-bis(dimethylamino)methane (1.26 ml, 7.41 mmol) and was heated to 100° C. with stirrng. After 0.5 h, the reaction mixture was allowed to cool and was triturated with petroleum ether (60–80) (15 ml). The resultant dark solid was then filtered off and dried in vacuo to give the title compound as a dark red solid (1.56 g, 92%).

$^1$H NMR (200 MHz, CDCl$_3$) δ(ppm): 8.18 (s, 1H), 8.12 (d, 1H), 6.40 (d, 1H), 3.08 (s, 6H), 2.58 (s, 3H).

Description 11

3-Chloro-6-(2-hydroxyethyl)-2-methylthio-5-nitropyridine (D11)

3-Chloro-6-[2-(dimethylamino)ethenyl]-2-methylthio-5-nitropyridine (D10) (1.05 g, 3.84 mmol) was dissolved in DME (40 ml) and treated with 2.5M hydrochloric acid (8 ml). After 15h, the reaction mixture was treated with solid sodium hydrogen carbonate until pH7 was reached. Water (20 ml) was then added and the resultant mixture was cooled to 0° C. Sodium borohydride (0.581 g, 15.36 mmol) was added portionwise over 2–3 minutes with stirring. After 0.5 h, water (200 ml) was added, and the reaction mixture was extracted with ethyl acetate (3×100 ml). The combined organic extracts were then dried (Na$_2$SO$_4$) and evaporated under reduced pressure to give a red/brown solid, which was purified by silica gel chromatography (3:1 petrol: EtOAc as eluant) to give the title compound as an orange solid (0.420 g, 44%).

$^1$H NMR (200 MHz, CDCl$_3$) δ(ppm): 8.78 (s, 1H), 4.15 (q, 2H), 3.48 (t, 2H), 2.68 (s, 3H), 2.60 (t, 1H).

Description 12

5-Amino-3-chloro-6-(2-hydroxyethyl)-2-methylthiopyridine (D12)

3-Chloro-6-(2-hydroxyethyl)-2-methylthio-5-nitropyridine (D11) (0.420 g, 1.69 mmol) was transformed to give the tide compound (0.306 g, 83%) as a cream solid according to the method described in Description 8.

$^1$H NMR (200 MHz, CDCl$_3$) δ(ppm): 7.00 (s, 1H), 4.14 (t, 2H), 3.70 (br s, 2H), 2.80 (t, 2H), 2.50 (s, 3H).

Description 13

N-3-[3-Chloro-6-(2-hydroxyethyl)-2-methylthio] pyridyl)-N'-(3-pyridyl)urea (D13)

5-Amino-3-chloro-6-(2-hydroxyethyl)-2-methylthiopyridine (D12) (0.300 g, 1.37 mmol) was transformed to give the title compound (0.32 g, 70%) as a yellow/brown solid according to the method described in Description 9.

$^1$H NMR (200 MHz, CDCl$_3$) δ(ppm): 9.42 (s, 1H), 8.62 (s, 1H), 8.42 (m, 1H), 8.23 (m, 2H), 7.97 (dt, 1H), 7.38 (dd, 1H), 4.90 (t, 1H), 3.87 (q, 2H), 2.95 (t, 2H), 2.52 (s, 10 3H)

EXAMPLE 1

N-3-Pyridyl-N'-5-(2-Thiomethyl-3-chloro)pyridyl urea (E1)

3-Chloro-2-thiomethylpyridine-5-carboxylic acid azide (D4) (0.33 g, 0.0014 mole) was heated under reflux in toluene (25 ml) under argon for 1 hour. After cooling to room temperature, 3-aminopyridine (0.11 g, 0.0014 mole) in dichloromethane (10 ml) was added and the mixture stirred at room temperature for 72 hours. The precipitated solid was filtered, washed with ether and dried in vacuo to leave the title compound (0.35 g, 85%) as an off white solid.

$^1$H NMR (270 MHz; D$_6$DMSO) δ: 2.49 (s,3H), 7.36 (q,1H) 7.95 (dd, 1H), 8.10 (d, 1H), 8.24(d,1H), 8.50 (d, 1H), 8.62 (d, 1H), 9.12 (s, 2H). MH$^+$295[C.I.]C$_{12}$H$_{11}$ ClN$_4$S.H$^+$ requires 295

EXAMPLE 2

4-Chloro-5-methylthio-2,3-dihydropyrrolo[2,3 c] pyridine-1-carboxylic acid pyridin-3-yl amide (E2)

N-3-[5chloro-4-(2-hydroxyethyl)-6-methylthio]pyridyl-N'-(3-pyridyl)urea (D9) (0.438 g, 1.29 mmol) was suspended in dry THF (45 ml) with stirring under argon, and was treated with triphenylphosphine (0.338 g, 1.29 mmol) and diethyl azodicarboxylate (0.203 ml, 1.29 mmol). Upon addition of the diethyl azodicarboxylate a clear pale yellow solution was produced. After 30 minutes, a white precipitate was produced, which was filtered off and recrystallised from ethanol to give the tide compound as a white solid (0.210 g, 51%). m.pt. 277°–278° C.

$^1$H NMR (250 MHz, CD$_3$SOCD$_3$) δ(ppm): 8.91 (s, 1H), 8.83 (s, 1H), 8.71 (d, 1H), 8.28 (dd, 1H), 8.00 (dt, 1H), 7.35 (dd, 1H), 4.22 (t, 2H), 3.28 (t, 2H), 2.50 (s, 3H).

EXAMPLE 3

6-Chloro-5-methylthio-2,3-dihydropyrrolo[3,2-b] pyridine-1-carboxylic acid pyridin-3-yl amide (E3)

N-3-[3-Chloro-6-(2-hydroxyethyl)-2-methylthio]pyridyl) -N'-(3-pyridyl)urea (D13) (0.300 g, 0.886 mmol) was transformed to give the title compound (0.020 g, 7%) as a white solid, according to the method described in Example 2. m.pt. 266°–267° C.

$^1$H NMR (270 MHz, CD$_3$SOCD$_3$) δ(ppm): 8.94 (s, 1H), 8.72 (d, 1H), 8.28 (dd, 1H), 8.04 (s, 1H), 7.97 (dt, 1H), 7.34 (dd, 1H), 4.22 (t, 2H), 3.30 (t, 2H), 2.50 (s, 3H).

Pharmacological data

[$^3$H]-mesulergine binding to rat or human 5-HT$_{2C}$ clones expressed in 293 cells in vitro Compounds can be tested following the procedure outlined in WO 94/04533.

The compounds of examples 1 to 3 have pKi values in the range 7.4 to 8.1.

We claim:

1. A compound of formula (1) or a salt thereof:

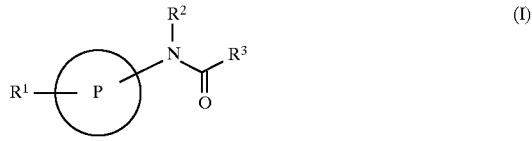

wherein: P1 represents phenyl, a quinoline or isoquinoline residue, or a 5-membered or 6-membered aromatic heterocyclic ring containing up to three heteroatoms selected from nitrogen, oxygen or sulphur;

R$^1$ is hydrogen, C$_{1-6}$ alkyl, C$_{1-6}$ alkylthio, cyano, nitro, halogen, CF$_3$, NR$^8$R$^9$, CONR$^8$R$^9$, CO$_2$R$^{10}$ or OR$^{10}$ where R$^8$, R$^9$ and R$^{10}$ are independently hydrogen, C$_{1-6}$ alkyl or aryl C$_{1-6}$ alkyl;

R$^2$ is hydrogen or C$_{16}$ alkyl;

R$^3$ is a group of formula (i):

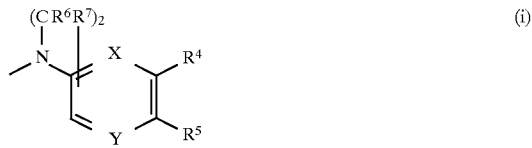

in which:

X and Y are both nitrogen or one is nitrogen and the other is carbon or a CH group;

R$^4$ and R$^5$ groups are independently C$_{1-6}$ alkyl optionally substituted by one or more halogen atoms, C$_{2-6}$ alkenyl, C$_{3-6}$ cycloalkyloxy, C$_{3-6}$ cycloalkylC$_{1-6}$ alkoxy, C$_{2-6}$ alkynyl, C$_{3-6}$ cycloalkyl, C$_{3-6}$ cycloalkyl-C$_{1-6}$ alkyl, C$_{1-6}$ alkylthio, C$_{3-6}$ cycloalkylthio, C$_{3-6}$ cycloalkyl-C$_{1-6}$ alkylthio, C1–6alkoxy, hydroxy, halogen, nitro, CF$_3$, C$_2$F$_5$, OCF$_3$, SCF$_3$, SO$_2$CF$_3$, SO$_2$F, formyl, C$_{2-6}$ alkanoyl, cyano, optionally substituted phenyl or thienyl, NR$^8$R$^9$, CONR$^8$R$^9$, or OR$^{10}$ where R$^8$, R$^9$ and R$^{10}$ are as defined for R$^1$, CO$_2$R$^{11}$ where R$^{11}$ is hydrogen or C$_{16}$ alkyl; or R$^4$ and R$^5$ form part of an optionally substituted 5-membered carbocyclic or heterocyclic ring;

R$^6$ and R$^7$ are independently hydrogen or C$_{1-6}$ alkyl; or $R^3$ is a group of formula (ii):

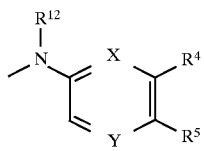

in which $R^4$ and $R^5$ are as defined in formula (i), X and Y are both nitrogen or one is nitrogen and the other is a CH group;
and $R^{12}$ is hydrogen or $C_{1-6}$ alkyl.

2. A compound according to claim 1 in which $R^1$ and $R^2$ are hydrogen.

3. A compound according to claim 1 in which $R^3$ is a group of formula (i).

4. A compound according to claim 1 in which $R^4$ is halogen and $R^5$ is $C_{1-6}$alkylthio.

5. A compound according to claim 1 in which P is pyridine.

6. A compound according to claim 1 which is:
N-3-Pyridyl-N'-5-(2-Thiomethyl-3-chloro)pyridyl urea,
4-Chloro-5-methylthio-2,3-dihydropyrrolopyridine-1-carboxylic acid pyridin-3-yl amide,
6-Chloro-5-methylthio-2,3-dihydropyrrolopyridine-1-carboxylic acid pyridin-3-yl amide,
and pharmaceutically acceptable salts thereof.

7. A pharmaceutical composition which comprises a compound according to claim 1 and a pharmaceutically acceptable carrier or excipient.

8. A process for the preparation of a compound of formula (I) as defined in claim 1 or a pharmaceutically acceptable salt thereof, which process comprises:

the coupling of a compound of formula (II);

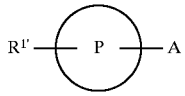

with a compound of formula (III):

B-R$^{3'}$       (III)

wherein P is as defined in formula (I), A and B contain the appropriate functional group(s) necessary to form the moiety —NR$^{2'}$ CO when couple, the variables $R^{1'}$, $R^{2'}$ and $R^{3'}$ are $R^1$, $R^2$ and $R^3$ respectively, as defined in formula (I), or groups convertible thereto, and thereafter optionally and as necessary and in any appropriate order, converting any $R^{1'}$, $R^{2'}$ and $R^{3'}$, when other $R^{1'}$, $R^{2'}$ and $R^{3'}$ respectively to $R^1$, $R^2$ and $R^3$, interconverting $R^1$, $R^2$ and $R^3$ and forming a pharmaceutically acceptable salt thereof.

9. A method of treatment of CNS and GI disorders which comprises administering to a sufferer a therapeutically effective amount of a compound of formula (I) as defined in claim 1 or a pharmaceutically acceptable salt thereof.

* * * * *